(12) United States Patent
Bush et al.

(10) Patent No.: US 11,090,404 B2
(45) Date of Patent: Aug. 17, 2021

(54) SYSTEMS FOR DISPENSING FLUID MATERIALS

(71) Applicant: The Procter & Gamble Company, Cincinnati, OH (US)

(72) Inventors: Stephan Gary Bush, Liberty Township, OH (US); Faiz Feisal Sherman, Mason, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 15/158,861

(22) Filed: May 19, 2016

(65) Prior Publication Data

US 2017/0333590 A1    Nov. 23, 2017

(51) Int. Cl.
*A61L 9/14* (2006.01)
*A61L 9/12* (2006.01)
(Continued)

(52) U.S. Cl.
CPC ............. *A61L 9/14* (2013.01); *A61L 9/125* (2013.01); *G06F 3/0484* (2013.01); *H04L 67/12* (2013.01);
(Continued)

(58) Field of Classification Search
CPC . B05B 12/02; B05B 12/1418; B05B 12/1472; A61L 9/14; A61L 2209/11;
(Continued)

(56) References Cited

U.S. PATENT DOCUMENTS

| 3,465,350 A | 9/1969 | Keur et al. |
| 3,465,351 A | 9/1969 | Keur et al. |

(Continued)

FOREIGN PATENT DOCUMENTS

| JP | 2006-280748 | 10/2006 |
| WO | WO 2003026458 A2 | 8/2003 |

(Continued)

OTHER PUBLICATIONS

U.S. Appl. No. 15/158,852, filed May 19, 2016, Stephan Gary Bush et al.

(Continued)

*Primary Examiner* — Cody J Lieuwen
(74) *Attorney, Agent, or Firm* — Sarah M DeCristofaro

(57) ABSTRACT

A system for dispensing fluid materials includes: a plurality of fluid storage chambers with each of the plurality containing a stored fluid; at least one MEMS dispensing element disposed in fluid communication with at least one of the plurality of fluid storage chambers; a control element disposed in electrical communication with the at least one MEMS dispensing element and comprising a memory component; a power supply disposed in electrical communication with the at least one MEMS dispensing element and the control element; and a user interface disposed in electrical communication with the control element. The memory component contains programmed instructions which, when executed by the control element cause the system to randomly dispense a first fluid from a first fluid storage chamber, and randomly disperse a second fluid from a second fluid storage chamber.

8 Claims, 3 Drawing Sheets

(51) Int. Cl.
*G06F 3/0484* (2013.01)
*H04L 29/08* (2006.01)

(52) U.S. Cl.
CPC ...... *A61L 2209/11* (2013.01); *A61L 2209/111* (2013.01); *A61L 2209/132* (2013.01); *A61L 2209/133* (2013.01); *A61L 2209/134* (2013.01)

(58) Field of Classification Search
CPC ......... A61L 2209/132; A61L 2209/133; G06F 3/0484; H04L 67/10
USPC .......................... 239/1, 61, 69, 70, 304–306
See application file for complete search history.

(56) References Cited

U.S. PATENT DOCUMENTS

| | | |
|---|---|---|
| 6,203,696 B1 | 3/2001 | Pearson |
| 6,325,475 B1 | 12/2001 | Hayes et al. |
| 6,371,451 B1 | 4/2002 | Choi |
| 6,622,723 B1 | 9/2003 | Nilsson et al. |
| 6,669,683 B2 | 12/2003 | Santini, Jr. et al. |
| 6,856,861 B2 | 2/2005 | Dirksing et al. |
| 6,986,442 B2 | 1/2006 | Engel et al. |
| 7,203,417 B2 | 4/2007 | Manne |
| 7,223,361 B2 | 5/2007 | Kvietok et al. |
| 7,223,362 B2 | 5/2007 | Kvietok |
| 7,718,119 B2 | 5/2010 | Tajima et al. |
| 8,158,083 B2 | 4/2012 | Krug et al. |
| 8,224,481 B2 | 7/2012 | Bylsma et al. |
| 8,403,915 B2 | 3/2013 | Santini, Jr. et al. |
| 8,585,308 B2 | 11/2013 | May |
| 2002/0053576 A1 | 5/2002 | Manne |
| 2002/0068010 A1 | 6/2002 | Laudamiel-Pellet et al. |
| 2004/0033171 A1 | 2/2004 | Kvietok |
| 2005/0124512 A1 | 6/2005 | Woo et al. |
| 2006/0000852 A1 | 1/2006 | Manne |
| 2007/0247555 A1 | 10/2007 | Diersing et al. |
| 2007/0253761 A1 | 11/2007 | May |
| 2008/0061163 A1* | 3/2008 | Kubby .................. A01M 1/205 239/102.1 |
| 2009/0185950 A1 | 7/2009 | Woo et al. |
| 2009/0261178 A1 | 10/2009 | Ivri et al. |
| 2010/0154791 A1 | 6/2010 | Ryan et al. |
| 2010/0294852 A1 | 11/2010 | Banco et al. |
| 2011/0068190 A1 | 3/2011 | Gasper |
| 2012/0104027 A1* | 5/2012 | Hoppe .................. A01M 1/026 222/1 |
| 2013/0037043 A1* | 2/2013 | Samain ............... G06F 19/3462 132/200 |
| 2013/0068853 A1* | 3/2013 | Hsiao ..................... B05B 17/06 239/11 |
| 2013/0134233 A1* | 5/2013 | Woo .................... A01M 1/2033 239/13 |
| 2014/0078229 A1 | 3/2014 | Jackson et al. |
| 2015/0019030 A1* | 1/2015 | Chandler ............. G05D 7/0629 700/283 |
| 2017/0076403 A1 | 3/2017 | Edwards et al. |
| 2017/0333589 A1 | 11/2017 | Bush et al. |

FOREIGN PATENT DOCUMENTS

| | | |
|---|---|---|
| WO | WO 200493929 | 11/2004 |
| WO | WO 2007053422 A1 | 5/2007 |
| WO | WO2007122583 A2 | 11/2007 |
| WO | WO 2013025768 A1 | 2/2013 |
| WO | WO 2014/043424 A1 | 3/2014 |
| WO | WO 2014043424 A1 | 3/2014 |
| WO | WO 2015/161250 A1 | 10/2015 |

OTHER PUBLICATIONS

International Search Report and Written Opinion dated Aug. 11, 2017, 12 pgs., U.S. Appl. No. 15/158,861.
International Search Report and Written Opinion dated Sep. 13, 2017, 12 pgs., U.S. Appl. No. 15/158,852.
All Office Actions, U.S. Appl. No. 15/158,852.

* cited by examiner

SYSTEMS FOR DISPENSING FLUID MATERIALS

FIELD OF THE INVENTION

The invention relates to methods and systems for the dispensing of fluids. The invention relates particularly to methods and systems for dispensing fluids in randomly determined quantities.

BACKGROUND OF THE INVENTION

The dispensing of fluids is well known, Systems for atomizing, misting or otherwise dispensing fluids into an environment are known. The dispensing of a combination of fluids is also known where two or more fluids are concurrently dispensed. One motivation for the combined dispensing of multiple fluids is to provide a system wherein the relative proportions of the members of the set of fluid may be altered. In the case of fragrances, where the fluids include fragrant oils, habituation to a single fragrance, or to a single combination of multiple fragrances may be avoided by varying the relative quantities of the respective fluids during dispensing. Varying the ratio of fluids according to a defined pattern provides a more complex pattern of fragrance but the more complex pattern may also lead to habituation as the overall set of fragrance possibilities may be relatively small and consistent.

What is needed is a system and method for dispensing multiple fluids such that the number of possible combinations of fluids, in terms of the relative proportions of fluids, is expanded and the nature of the respective combinations is less predictable.

SUMMARY OF THE INVENTION

In one aspect a system for dispensing fluid materials includes: a plurality of fluid storage chambers with each of the plurality containing a stored fluid; at least one MEMS dispensing element disposed in fluid communication with at least one of the plurality of fluid storage chambers; a control element disposed in electrical communication with the at least one MEMS dispensing element and comprising a memory component; a power supply disposed in electrical communication with the at least one MEMS dispensing element and the control element; and a user interface disposed in electrical communication with the control element. The memory component contains programmed instructions which, when executed by the control element cause the system to randomly dispense a first fluid from a first fluid storage chamber, and randomly disperse a second fluid from a second fluid storage chamber.

In one aspect, a method for dispensing a multi-component fluid includes providing a system for dispensing fluids which includes: a plurality of fluid storage chambers, each of the fluid storage chambers containing a stored fluid; at least one MEMS dispensing element disposed in fluid communication with at least one fluid storage chamber; a control element disposed in electrical communication with the at least one MEMS dispensing element and including a second memory component; a power supply disposed in electrical communication with the at least one MEMS dispensing element and the control element; and a user interface disposed in electrical communication with the control element. The memory component contains programmed instructions which, when executed by the control element cause the system to dispense a first fluid from a first fluid storage chamber at a first dispensing rate, and a second fluid from a second fluid storage chamber at a second dispensing rate. The method also includes determining the content of the first memory component data; and randomly dispensing a first and second fluid from the fluid storage chambers.

DETAILED DESCRIPTION OF THE INVENTION

Ink Jet Head

Figure 1:
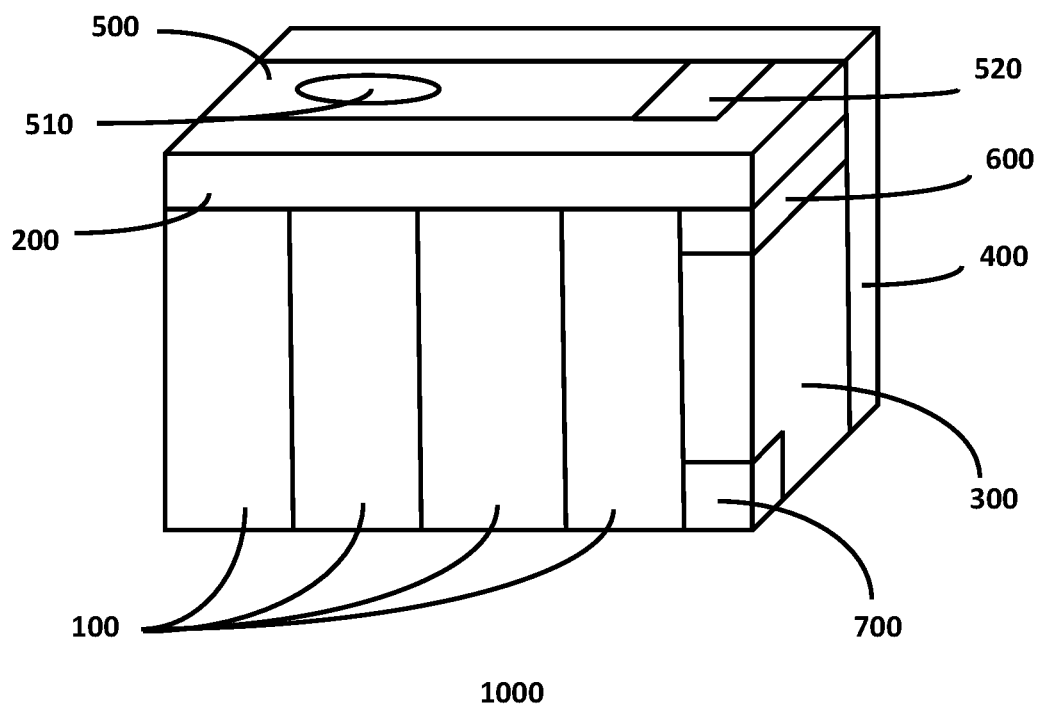
FIG. 1 provides a schematic illustration of one embodiment of the invention system.

The delivery system of the present invention employs an ink jet head typically used in ink jet printing. There are two major categories of ink jet printing: "drop-on-demand" and "continuous" ink jet printing.

For continuous ink jet printing, an ink is supplied under pressure to an ink jet nozzle and forced out through a small orifice. Prior to passing out of the nozzle, the pressurized ink stream proceeds through a ceramic crystal which is subjected to an electric current. This current causes a piezoelectric vibration equal to the frequency of the AC electric current. This vibration, in turn, generates the ink droplets from the unbroken ink stream. The ink stream breaks up into a continuous series of drops which are equally spaced and of equal size. Surrounding the jet, at a point where the drops separate from the fluid stream in a charge electrode, a voltage is applied between the charge electrode and the drop stream. When the drops break off from the stream, each drop carries a charge proportional to the applied voltage at the instant at which it breaks off. By varying the charge electrode voltages at the same rate as drops are produced, it is possible to charge every drop to a predetermined level. The drop stream continues its flight and passes between two deflector plates which are maintained at a constant potential. In the presence of this field, a drop is deflected towards one of the plates by an amount proportional to the charge carried. Drops which are uncharged are undeflected and collected into a gutter to be recycled to the ink nozzle. Those drops which are charged, and hence deflected, impinge on a substrate traveling at a high speed at right angles to the direction of drop deflection. By varying the charge on individual drops, the desired pattern can be printed.

In a typical "drop-on-demand" ink jet printing process, a fluid ink is forced under pressure through a very small orifice of a diameter typically about 0.0024 inches (5-50 microns) in the form of minute droplets by rapid pressure impulses. The rapid pressure impulses are typically generated in the print head by either expansion of a piezoelectric crystal vibrating at a high frequency or volatilization of a volatile composition (e.g. solvent, water, propellant) within the ink by rapid heating cycles. The piezoelectric crystal expansion causes the ink to pass through the orifice as minute droplets in proportion to the number of crystal vibrations. Thermal ink jet printers employ a heating element within the print head to volatilize a portion of the composition that propels the vast majority of fluid through the orifice nozzle to form droplets in proportion to the number of on-off cycles for the heating element. The ink is forced out of the nozzle when needed to print a spot on a substrate as part of a desired image. The minute droplets may be energized to achieve an electrical charge and deflected as in the continuous ink jet printing. Conventional ink jet printers are more particularly described in U.S. Pat. Nos. 3,465,350 and 3,465,351.

Another type of ink jet printing process is an electrostatic ink jet process which employs an electrostatic field to draw the ink through the nozzle to the substrate. Charged ink droplets are drawn to an oppositely charged platen behind the receiving substrate. Such devices have been developed by Technology International Corp. of Boulder, Colo., under the trade name ESIJET.

While the present invention may employ any of the above described ink jet head delivery processes, the ink jet head of the present invention may include a membrane of 8 to 48 nozzles, alternatively 8 to 32 nozzles, alternatively 8 to 16 nozzles, alternatively 8 to 12 nozzles, that delivers 1-100 picoliters of fluid composition per nozzle, alternatively 1-2 picoliters per nozzle on an ink jet head that may be less than about 25 mm$^2$. In some embodiments, the ink jet head delivers from about 1 mg to about 1000 mg of fluid composition per hour into the air. One type of membrane suitable for the present invention is an integrated membrane of nozzles obtained via MEMS technology as described in US 2010/0154790. The MEMS head of the invention may comprise a thermal driver or a piezo mechanical driver. A thermal MEMS heats a fluid present in a chamber to a point where at least part of the fluid boils and leaves the chamber carrying the remaining portion of the fluid with it. A piezo MEMS driver vibrates mechanically and drives the composition from the chamber.

Reservoir

The delivery system includes a reservoir for containing the fluid composition, such as illustrated in FIGS. 1-3. In some embodiments, the reservoir is configured to contain from about 0.2 to about 50 ml of fluid composition, alternatively from about 10 to about 30 ml of fluid composition, alternatively from about 15 to about 20 ml of fluid composition. The delivery system may be configured to have 10 multiple reservoirs, each containing the same or a different composition. Each of the multiple reservoirs may be an independent article, or the multiple reservoirs may be a single multi-chamber article. The reservoir may be formed as a separate construction, so as to be removable from the overall system and replaceable (e.g. a refill). The reservoir can be made of any suitable material for containing a fluid composition. Suitable materials for the containers include, but are 15 not limited to, glass and plastic. Examples of such reservoirs are readily available in the marketplace.

The reservoir may comprise a capillary element made of any commercially available wicking material such as a fibrous or porous wick that contains multiple interconnected open cells which form capillary passages to draw a fluid composition up from the reservoir to come in contact with the fluid feed of the ink jet engine. Non-limiting examples of suitable compositions for the capillary element include polyethylene, ultra-high molecular weight polyethelene (UHMW), nylon 6 (N6), polypropylene (PP), polyester fibers, ethyl vinyl acetate, polyether sulfone, polyvinylidene fluoride (PVDF), and polyethersulfone (PES), polytetrafluroethylene (PTFE), and combinations thereof.

In some embodiments, the capillary element may be a high density wick composition to aid in containing the scent of a perfume mixture. In one embodiment, the capillary element is made from a plastic material chosen from high-density polyethylene (HDPE). As used herein, high density wick compositions include any conventional wick material known in the art having a pore diameter or equivalent pore diameter (e.g. in the case of fiber based wicks) ranging from about 20 microns to about 150 microns, alternatively from about 30 microns to about 70 microns, alternatively from about 30 microns to about 50 microns, alternatively, about 40 microns to about 50 microns.

In some embodiments, the capillary element is free of a polyurethane foam. Many ink jet cartridges use an open cell polyurethane foam which can be incompatible with perfume mixtures over time (e.g. after 2 or 3 months) and can break down. Regardless of the material of manufacture, the capillary element can exhibit an average pore size from about 10 microns to about 500 microns, alternatively from about 50 microns to about 150 microns, alternatively about 70 microns. The average pore volume of the wick is from about 15% to about 85%, alternatively from about 25% to about 50%. Good results have been obtained with wicks having an average pore volume of about 38%. The capillary element can also be of variable length, such as, from about 1 mm to about 100 mm, or from about 5 mm to about 75 mm, or from about 10 mm to about 50 mm.

The capillary element is in fluid communication with the fluid composition and may extend at least partially outside the reservoir. In some embodiments, the capillary element may be completely surrounded by the walls of the reservoir. Depending upon the configuration of the delivery system, a fluid composition may travel up or down the capillary element. After flowing from the reservoir, the fluid composition may continue traveling downstream to a holding tank from which the ink jet head draws fluid from to atomize the fluid into the air.

In some embodiments, the delivery system may include a fluid channel positioned in a flow path between the capillary element and the holding tank. A channel may be useful in configurations where the reservoir and holding tank are placed laterally from one another. The length of the channel, measured from the capillary element to center of the reservoir, may be about 12 mm, alternatively about 13 mm, alternatively, about 14 mm, alternatively about 15 mm, alternatively about 11 mm, alternatively about 10 mm.

Fluid Composition

To operate satisfactorily within an ink jet delivery system, many characteristics of a fluid composition are taken into consideration. Some factors include formulating fluids with viscosities that are optimal to emit from the ink jet head, formulating fluids with limited amounts or no suspended solids that would clog the ink jet head, formulating fluids to be sufficiently stable to not dry and clog the ink jet head, etc. Operating satisfactorily within an ink jet deli very system, however, addresses only some of the requirements necessary for a fluid composition having more than 50 wt % of a perfume mixture to atomize properly from an ink jet delivery system and to be delivered effectively as an air freshening or malodor reducing composition.

The fluid composition of the present invention may exhibit a viscosity of less than 10,000 centipoise ("cps"), alternatively less than 5000 cps, alternatively less than 2500 cps, alternatively from about 1 cps to about 2500 cps. In one embodiment, a viscosity of between about 1 and about 1000 cps, alternatively between about 1 and about 500 cps, or between about 1 and about 250 cps, or about 100 cps, or about 50 cps. And, the volatile composition may have surface tensions below about 35, alternatively from about 20 to about 30 dynes per centimeter. Viscosity is in cps, as determined using the Bohlin CVO Rheometer system in conjunction with a high sensitivity double gap geometry.

In some embodiments, the fluid composition is free of suspended solids or solid particles existing in a mixture wherein particulate matter is dispersed within a liquid matrix. Free of suspended solids is distinguishable from dissolved solids that are characteristic of some perfume materials.

The fluid composition of the present invention comprises a perfume mixture present in an amount greater than about 50%, by weight of the fluid composition, alternatively greater than about 60%, alternatively greater than about 70%, alternatively greater than about 75%, alternatively greater than about 80%, alternatively from about 50% to about 100%, alternatively from about 60% to about 100%, alternatively from about 70% to about 100%, alternatively from about 80% to about 100%, alternatively from about 90% to about 100%. In some embodiments, the fluid composition may consist entirely of the perfume mixture (i.e. 100 wt. %).

In one embodiment, the fluid composition of the system may comprise between about 50% and 100% of an active mixture. The active mixture has a vapor pressure of less than about 2.3 kPa at 20 C. The fluid composition further comprises between about 0% and about 50% of a carrier. The carrier has a vapor pressure of greater than about 2.3 kPa at 20 C.

The perfume mixture may contain one or more perfume materials. The perfume materials are selected based on the material's boiling point ("B.P."). The B.P. referred to herein is measured under normal standard pressure of 760 mm Hg. The B.P. of many perfume ingredients, at standard 760 mm Hg can be found in "Perfume and Flavor Chemicals (Aroma Chemicals)," written and published by Steffen Arctander, 1969.

In the present invention, the perfume mixture may have a B.P. of less than 250° C., alternatively less than 225° C., alternatively less than 200° C., alternatively less than about 150° C., alternatively less than about 120° C., alternatively less than about 100° C., alternatively about 50° C. to about 200° C., alternatively about 110° C. to about 140° C. In some embodiments, about 3 wt % to about 25 wt % of the perfume mixture has a B.P. of less than 200° C., alternatively about 5 wt % to about 25 wt % of the perfume mixture has a B.P. of less than 200° C.

Table 1 lists some non-limiting, exemplary individual perfume materials suitable for the perfume mixture of the present invention.

TABLE 1

| CAS Number | Perfume Raw Material Name | B.P. (° C.) |
| --- | --- | --- |
| 105-37-3 | Ethyl propionate | 99 |
| 110-19-0 | Isobutyl acetate | 116 |
| 928-96-1 | Beta gamma hexenol | 157 |
| 80-56-8 | Alpha Pinene | 157 |
| 127-91-3 | Beta Pinene | 166 |
| 1708-82-3 | cis-hexenyl acetate | 169 |
| 124-13-0 | Octanal | 170 |
| 470-82-6 | Eucalyptol | 175 |
| 141-78-6 | Ethyl acetate | 77 |

Table 2 shows an exemplary perfume mixture having a total B.P. less than 200° C.

TABLE 2

| CAS Number | Perfume Raw Material Name | Wt % | B.P. (° C.) |
| --- | --- | --- | --- |
| 123-68-2 | Allyl Caproate | 2.50 | 185 |
| 140-11-4 | Benzyl Acetate | 3.00 | 214 |
| 928-96-1 | Beta Gamma Hexenol | 9.00 | 157 |
| 18479-58-8 | Dihydro Myrcenol | 5.00 | 198 |
| 39255-32-8 | Ethyl 2 Methyl Pentanoate | 9.00 | 157 |
| 77-83-8 | Ethyl Methyl Phenyl Glycidate | 2.00 | 260 |
| 7452-79-1 | Ethyl-2-Methyl Butyrate | 8.00 | 132 |
| 142-92-7 | Hexyl Acetate | 12.50 | 146 |
| 68514-75-0 | Orange Phase Oil 25X1.18%-Low Cit. 14638 | 10.00 | 177 |
| 93-58-3 | Methyl Benzoate | 0.50 | 200 |
| 104-93-8 | Para Cresyl Methyl Ether | 0.20 | 176 |
| 1191-16-8 | Prenyl Acetate | 8.00 | 145 |
| 88-41-5 | Verdox | 3.00 | 223 |
| 58430-94-7 | Iso Nonyl Acetate | 27.30 | 225 |
| | TOTAL: | 100.00 | |

When formulating fluid compositions for the present invention, one may also include solvents, diluents, extenders, fixatives, thickeners, or the like. Non-limiting examples of these materials are ethyl alcohol, carbitol, diethylene glycol, dipropylene glycol, diethyl phthalate, triethyl citrate, isopropyl myristate, ethyl cellulose, and benzyl benzoate.

In some embodiments, the fluid composition may contain functional perfume components ("FPCs"). FPCs are a class of perfume raw materials with evaporation properties that are similar to traditional organic solvents or volatile organic compounds ("VOCs"). "VOCs", as used herein, means volatile organic compounds that have a vapor pressure of greater than 0.2 mm Hg measured at 20° C. and aid in perfume evaporation. Exemplary VOCs include the following organic solvents: dipropylene glycol methyl ether ("DPM"), 3-methoxy-3-methyl-1-butanol ("MMB"), volatile silicone oil, and dipropylene glycol esters of methyl, ethyl, propyl, butyl, ethylene glycol methyl ether, ethylene glycol ethyl ether, diethylene glycol methyl ether, diethylene glycol ethyl ether, or any VOC under the tradename of Dowanol™ glycol ether. VOCs are commonly used at levels greater than 20% in a fluid composition to aid in perfume evaporation.

The FPCs of the present invention aid in the evaporation of perfume materials and may provide a hedonic, fragrance benefit. FPCs may be used in relatively large concentrations without negatively impacting perfume character of the overall composition. As such, in some embodiments, the fluid composition of the present invention may be substantially free of VOCs, meaning it has no more than 18%, alternatively no more than 6%, alternatively no more than 5%, alternatively no more than 1%, alternatively no more than 0.5%, by weight of the composition, of VOCs. The volatile composition, in some embodiments, may be free of VOCs.

Perfume materials that are suitable as a FPC may have a KI, as defined above, from about 800 to about 1500, alternatively about 900 to about 1200, alternatively about 1000 to about 1100, alternatively about 1000.

Perfume materials that are suitable for use as a FPC can also be defined using odor detection threshold ("ODT") and non-polarizing scent character for a given perfume character scent camp. ODTs may be determined using a commercial GC equipped with flame ionization and a sniff-port. The GC is calibrated to determine the exact volume of material injected by the syringe, the precise split ratio, and the hydrocarbon response using a hydrocarbon standard of known concentration and chain-length distribution. The air flow rate is accurately measured and, assuming the duration of a human inhalation to last 12 seconds, the sampled volume is calculated. Since the precise concentration at the detector at any point in time is known, the mass per volume inhaled is known and concentration of the material can be calculated. To determine whether a material has a threshold below 50 ppb, solutions are delivered to the sniff port at the back-calculated concentration. A panelist sniffs the GC effluent and identifies the retention time when odor is noticed. The average across all panelists determines the threshold of noticeability. The necessary amount of analyte is injected onto the column to achieve a 50 ppb concentration at the detector. Typical GC parameters for determining ODTs are listed below. The test is conducted according to the guidelines associated with the equipment.

Equipment:
GC: 5890 Series with FID detector (Agilent Technologies, Ind., Palo Alto, Calif., USA);
7673 Autosampler (Agilent Technologies, Ind., Palo Alto, Calif., USA);
Column: DB-1 (Agilent Technologies, Ind., Palo Alto, Calif., USA) Length 30 meters ID 0.25 mm film thickness 1 micron (a polymer layer on the inner wall of the capillary tubing, which provide selective partitioning for separations to occur).

Method Parameters:
Split Injection: 17/1 split ratio;
Autosampler: 1.13 microliters per injection;
Column Flow: 1.10 mL/minute;
Air Flow: 345 mL/minute;
Inlet Temp. 245° C.;
Detector Temp. 285° C.
Temperature Information:
Initial Temperature: 50° C.;
Rate: 5 C/minute;
Final Temperature: 280° C.;
Final Time: 6 minutes;
Leading assumptions:
(i) 12 seconds per sniff
(ii) GC air adds to sample dilution.

FPCs may have an ODT from greater than about 1.0 parts per billion ("ppb"), alternatively greater than about 5.0 ppb, alternatively greater than about 10.0 ppb, alternatively greater than about 20.0 ppb, alternatively greater than about 30.0 ppb, alternatively greater than about 0.1 parts per million.

In one embodiment, the FPCs in a fluid composition of the present invention may have a KI in the range from about 900 to about 1400; alternatively from about 1000 to about 1300. These FPCs can be either an ether, an alcohol, an aldehyde, an acetate, a ketone, or mixtures thereof.

FPCs may be highly volatile, low B.P. perfume materials. Exemplary FPC include iso-nonyl acetate, dihydro myrcenol (3-methylene-7-methyl octan-7-ol), linalool (3-hydroxy-3, 7-dimethyl-1, 6 octadiene), geraniol (3, 7 dimethyl-2, 6-octadien-1-ol), d-limonene (1-methyl-4-isopropenyl-1-cyclohexene, benzyl acetate, isopropyl mystristate, and mixtures thereof. Table 3 lists the approximate reported values for exemplary properties of certain FPCs.

TABLE 3

| FPC | B.P. (° C.) | MW | Clog P @ 25° C. | Flash point (° C.) | Vapor pressure | KI | ODT |
|---|---|---|---|---|---|---|---|
| Iso-Nonyl Acetate (CAS# 58430-94-7) | 225 | 186.3 | 4.28 | 79.4 | 0.11 | 1178 | 12 ppb |
| Dihydro Myrcenol (CAS# 18479-58-8) | 198 | 156.3 | 3.03 | 76.1 | 0.1 | 1071 | 32 ppb |
| Linalool (CAS# 78-70-6) | 205 | 154.3 | 2.549 | 78.9 | 0.05 | 1107 | 22 ppb |
| Geraniol (CAS# 106-24-1) | 237 | 154.3 | 2.769 | 100 | 0.00519 | 1253 | 0.4 ppb |
| D-Limonene (CAS# 94266-47-4) | 170 | 136 | 4.35 | 47.2 | 1.86 | 1034 | 204 ppb |

The total amount of FPCs in the perfume mixture may be greater than about 50%, alternatively greater than about 60%, alternatively greater than about 70%, alternatively greater than about 75%, alternatively greater than about 80%, alternatively from about 50% to about 100%, alternatively from about 60% to about 100%, alternatively from about 70% to about 100%, alternatively from about 75% to about 100%, alternatively from about 80% to about 100%, alternatively from about 85% to about 100%, alternatively from about 90% to about 100%, alternatively about 100%, by weight of the perfume mixture. In some embodiments, the perfume mixture may consist entirely of FPCs (i.e. 100 wt. %).

For purposes of illustrating the present invention in further detail, Table 4 lists a non-limiting, exemplary fluid composition comprising FPCs and their approximate reported values for KI and B.P.

TABLE 4

| Material Name | KI | wt. % | B.P. (° C.) |
|---|---|---|---|
| Benzyl Acetate (CAS # 140-11-4) | 1173 | 1.5 | 214 |
| Ethyl-2-methyl Butyrate (CAS # 7452-79-1) | 850 | 0.3 | 132 |
| Amyl Acetate (CAS # 628-63-7) | 912 | 1.0 | 149 |
| Cis 3 Hexenyl Acetate (CAS # 3681-71-8) | 1009 | 0.5 | 169 |
| Ligustral (CAS # 27939-60-2) | 1094 | 0.5 | 177 |
| Melonal (CAS # 106-72-9) | 1060 | 0.5 | 116 |
| Hexyl Acetate (CAS # 142-92-7) | 1016 | 2.5 | 146 |
| Dihydro Myrcenol (CAS# 18479-58-8) | 1071 | 15 | 198 |
| Phenyl Ethyl Alcohol (CAS# 60-12-8) | 1122 | 8 | 219 |
| Linalool (CAS # 78-70-6) | 1243 | 25.2 | 205 |
| Geraniol (CAS# 106-24-1) | 1253 | 5 | 238 |
| Iso Nonyl Acetate (CAS# 40379-24-6) | 1295 | 22.5 | 225 |
| Benzyl Salicylate (CAS # 118-58-1) | 2139 | 3 | 320 |
| Coumarin (CAS # 91-64-5) | 1463 | 1.5 | 267 |
| Methyl Dihydro Jasmonate (CAS# 24851-98-7) | 1668 | 7 | 314 |
| Hexyl Cinnamic Aldehyde (CAS # 101-86-0) | 1770 | 6 | 305 |

It is contemplated that the fluid composition may comprise other volatile materials in addition to or in substitution for the perfume mixture including, but not limited to, volatile dyes; compositions that function as insecticides; essential oils or materials that acts to condition, modify, or otherwise modify the environment (e.g. to assist with sleep, wake, respiratory health, and like conditions); deodorants or malodor control compositions (e.g. odor neutralizing materials such as reactive aldehydes (as disclosed in U.S. 2005/0124512), odor blocking materials, odor masking materials, or sensory modifying materials such as ionones (also disclosed in U.S. 2005/0124512)).

Optional Features

Fan

In another aspect of the invention, the delivery system may comprise a fan to assist in driving room-fill and to help avoid deposition of larger droplets from landing on surrounding surfaces that could damage the surface. The fan may be any known fan used in the art for air freshening systems that delivers 1-1000 cubic centimeters of air/minute, alternatively 10-100 cubic centimeters/minute.

Sensors

In some embodiments, the delivery system may include commercially available sensors that respond to environmental stimuli such as light, noise, motion, and/or odor levels in the air. For example, the delivery system can be programmed to turn on when it senses light, and/or to turn off when it senses no light. In another example, the delivery system can turn on when the sensor senses a person moving into the vicinity of the sensor. Sensors may also be used to monitor the odor levels in the air. The odor sensor can be used to turn-on the delivery system, increase the heat or fan speed, and/or step-up the delivery of the fluid composition from the delivery system when it is needed.

The sensor may also be used to measure fluid levels in the reservoir to indicate the reservoir's end-of-life in advance of depletion. In such case, an LED light may turn on to indicate the reservoir needs to be filled or replaced with a new reservoir.

The sensors may be integral with the delivery system housing or in a remote location (i.e. physically separated from the delivery system housing) such as remote computer or mobile smart device/phone. The sensors may communicate with the delivery system remotely via low energy blue tooth, 6 low pan radios or any other means of wirelessly communicating with a device and/or a controller (e.g. smart phone or computer).

Portable/Battery

The delivery system may be configured to be compact and easily portable. In such case, the delivery system may be battery operated. The delivery system may be capable for use with electrical sources as 9-volt batteries, conventional dry cells such as "A", "AA", "AAA", "C", and "D" cells, button cells, watch batteries, solar cells, as well as rechargeable batteries with recharging base.

Programming

Figure 2:
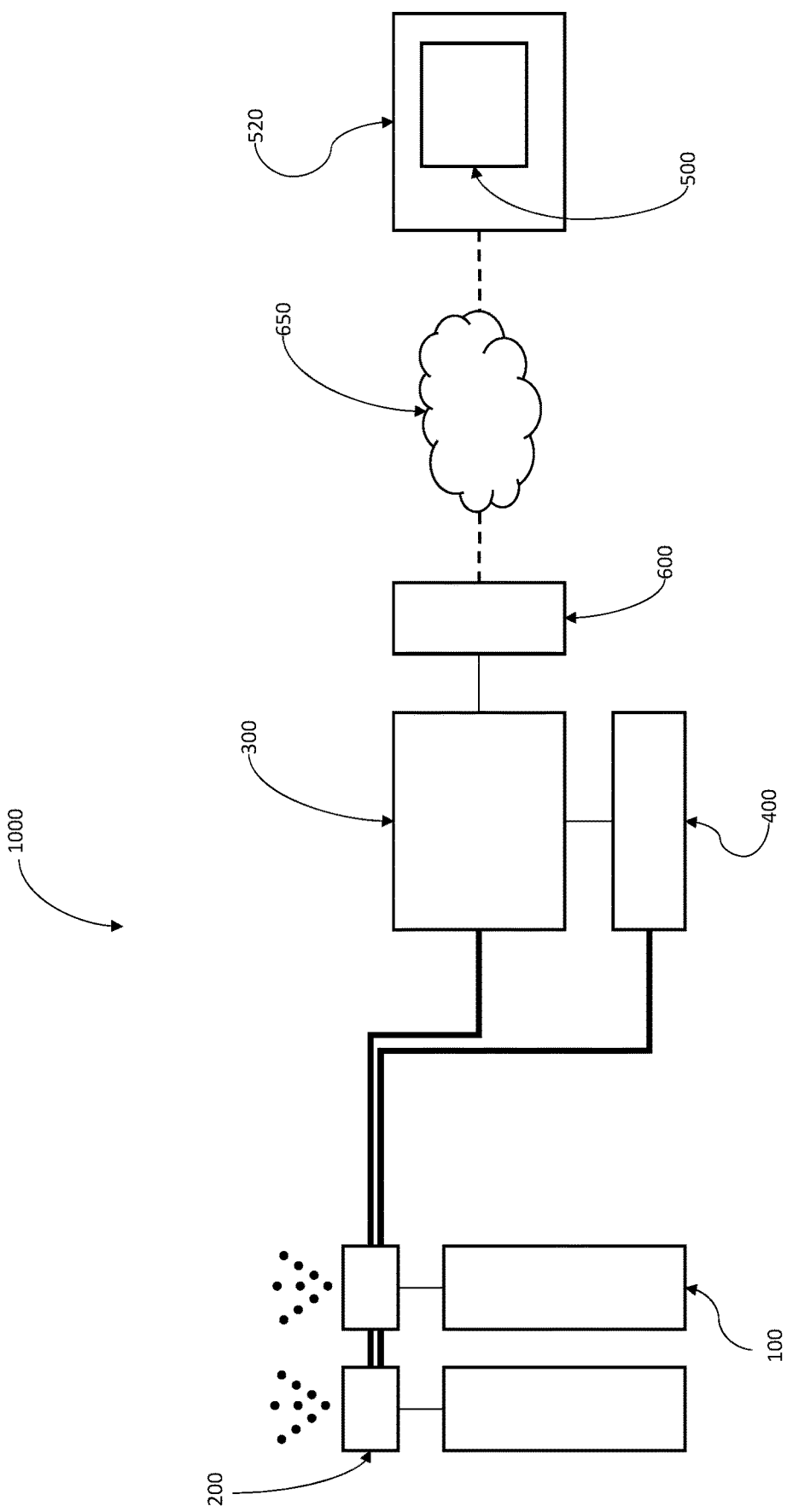
FIG. 2 illustrates a schematic diagram of an embodiment of the system.
Figure 3:
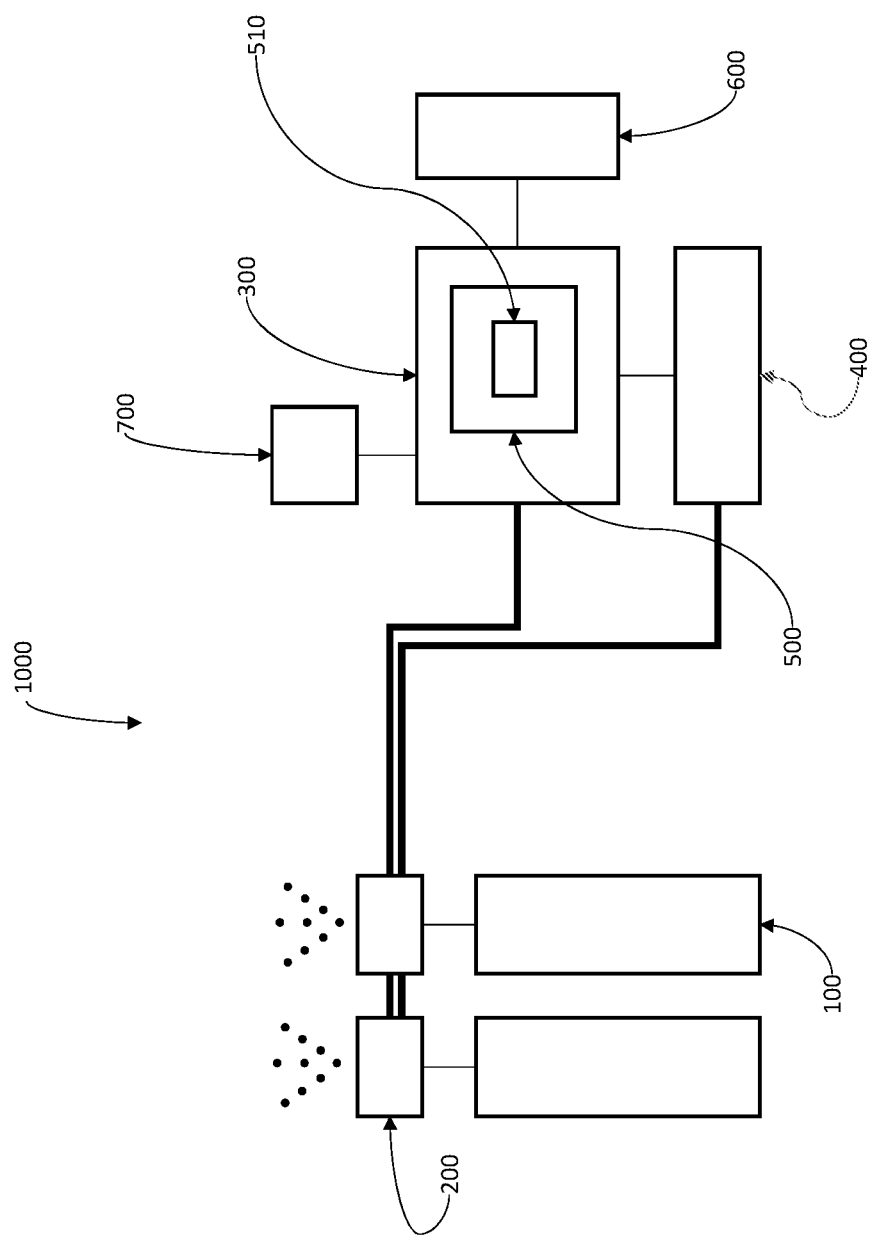
FIG. 3 illustrates a schematic diagram of an embodiment of the system.

The delivery system may include a control element with programmable electronics to set a precise intensity level and delivery rate (in milligrams per hour), such as illustrated in FIGS. 1-3. Alternatively, the control circuitry of the delivery system may allow a user to adjust the intensity and/or the timing of the delivering the fluid composition for personal preference, efficacy, or for room size. For example, the delivery system may provide 5 intensity levels for a user to select and user selected options of 25 delivering the fluid composition every 6, 12, or 24 hours.

In multiple reservoir delivery systems, a microprocessor and timer could be installed to emit the fluid composition from individual reservoirs at different times and for selected time periods, including emitting the volatile compositions in an alternating emission pattern as described in U.S. Pat. No. 7,223,361. Additionally, the delivery system could be programmable so a user can select certain compositions for emission. In the case of scented perfumes being emitted simultaneously, a customized scent may be delivered to the air.

In one embodiment, the multiple reservoir system may be programmed to include a random number generating function in determining the emission pattern and/or the frequency of firing of the nozzles for at least one fluid of the composition. In such an embodiment, the parameters associated each firing of the dispensing system may be altered and randomly selected to introduce variation into the overall composition and scent perceived by those in the vicinity of the system or observing the deposition pattern of fluids upon a substrate.

The dispensing or dispersion of a random amount of a fluid or combination of fluids into an environment or onto a substrate refers to an outcome wherein at least one fluid is dispersed according a set of randomly selected operating parameters controlling the dispensing system. The parameters may be selected using the control elements of the system in conjunction with random number generation functions to select a set of parameter values which is random while each element of the set remains within the working range of values for that parameter. In one embodiment, the control element may include programming for the calculation of delivery parameter values to generate a relatively random delivery of the fluids by the system. For example, the relative ratios of different fluids may be altered, the droplet size of fluids may be altered, the firing frequencies may be altered, and the nozzle patterns for fluid dispensing may be subject to random determination to achieve variation in the overall dispensing of the system.

In one embodiment, the system for dispensing fluid materials may include: a plurality of fluid storage chambers, each of the plurality containing a stored fluid; at least one MEMS dispensing element, as described above, disposed in fluid communication with at least one of the plurality of fluid storage chambers; a control element disposed in electrical communication with the at least one MEMS dispensing element and comprising a memory component; a power supply disposed in electrical communication with the at least one MEMS dispensing element and the control element; a user interface disposed in electrical communication with the control element; wherein the memory component contains programmed instructions which, when executed by the control element cause the system to randomly dispense a first fluid from a first fluid storage chamber, and randomly disperse a second fluid from a second fluid storage chamber, or reservoir.

The power supply of the system provides a regulated source of electrical power to drive the control sensing and dispensing functions. The power supply may be an AC or DC supply. Portable systems may include one or more batteries serving as the power supply. In one embodiment, the system may be plugged directly into a typical wall outlet and driven by standard AC line power. Alternatively, the AC may be transformed by an internal or external transformer to yield DC power in line with the particular needs of the system.

The random nature of the fluid dispensing may refer to the quantity of the respective fluids as well as the disposition, or dispersion, of the fluids. The random nature may be achieved by incorporating a random number function into the calculation of the operating frequency to be used for a particular firing event as well as by randomly selecting a nozzle pattern either from a pre-defined listing of potential nozzle patterns, or by using a random number generator in a function to compile a selection of nozzles to be fired for a particular event.

In one embodiment, the user interface comprises a switch in electrical communication with an input of the control element. In such an embodiment, any form of electrical switch may be used including momentary and maintained contact switches, single-pole switches, membrane switches and other suitable switch elements as are known to those of skill in the art. The switch may be used to alter the electrical state of an input of the control element. The control element may contain logic configured to read and execute the programmed instructions of the memory component as, or after, the input electrical state changes. The programmed instructions may include randomization calculations as described above.

The user interface may include a selector switch having multiple positions rather than simply two positions. The selector may be a physical selector or a virtual selector provided as part of a device interface including a graphical display including parameter selection menus and input keys for identifying and selecting menu options. In such an embodiment, the memory component of the system may include a plurality of pre-programmed instruction sets and the menu or selector switch may be used to choose which set of instructions should be executed. Alternatively, the user interface may allow the selection of an option wherein the system will randomly select from the plurality of instruction sets for each dispensing instance.

In one embodiment, the system may include a network interface disposed in electrical communication with the power supply and the control element. Exemplary network interface hardware includes: the CC3100 network processor available from Texas Instruments Inc. of Dallas, Tex. for wireless communication compatible with IEEE standards 802.11b, 802.11g, 802.11n (commonly referred to as Wi-Fi® by the Wi-Fi Alliance®), the BlueNRG-MS network processor available from STMicroelectronics, N.V. of Geneva, Switzerland for wireless communication compatible with the Bluetooth Smart (or Bluetooth Low Energy) as defined by revision 4.1 of the Bluetooth specification published by Bluetooth SIG, Inc., or the CC2630 system-on-chip with IEEE 802.15.4 compatible radio capable of providing wireless communication compatible with ZigBee® application profiles as published by the ZigBee Alliance.

In one embodiment, the user interface of the system may be incorporated into an application resident upon and executed by a networked device such as a smart device or phone. The application may then utilize the computing and communication elements of the device to communicate not only with the dispensing system but also with other devices over a WiFi or other wireless or wired communications network. The device may provide information associated both with the dispensing system and the device itself such as date and time, location, local temperature, and other information available to the device internally. The system may transfer instructions sets or dispensing parameters from the networked device to the control element memory element for use in dispensing fluids.

In one embodiment, the reservoirs may comprise a memory or other readable element and the system may include a reading element adapted to evaluate the contents of the reservoir memory element. The output of the reader may be provided to the control element and to the networked device to be used as input in determining the nature of the dispensing parameters calculated or selected for a dispensing event. The reservoir memory may contain information associated with the fluid contained in the reservoir.

In practice, the provided system may be used by interacting with the user interface thereby causing the system to execute stored programming resulting in the random dispensing of at least one of the plurality of fluid available.

In one embodiment, the system may further read the contents of memory associated with a reservoir and incorporate the contents into the instructions for randomly dispensing the fluid(s). In such an embodiment, the reservoir memory contents may be used to select a particular set, or subset, of pre-programmed instructions available to the control element. The reservoir may comprise indicia in combination with memory or as an alternative to memory. In one embodiment, the reservoir may comprise indicia associated with the fluid contained in the reservoir. In this embodiment, the system may recognize the indicia, associate the recognized indicia with a particular fluid and select appropriate instructions, or alter the system instructions in response to the recognized presence of the fluid.

The user interface may allow a user to alter a portion of the contents of the control element memory such that the dispensing of the fluids is also altered. Exemplary alterations include relative proportional ranges for the respective fluid, the timing of fluid dispensing, the volume of fluid(s) to be dispensed. Each of these and other parameters may be specified as a desirable or acceptable range of values and the control element may then be used to randomly define a value within the specified ranges for a particular dispensing event. The system may then utilize the altered memory values in the dispensing of fluid(s).

The user interface may be utilized to provide input requesting a sample dispensing according to a selected set of parameters or range of parameters. In this manner, the user may determine if the values or ranges defined through the interface are acceptable prior to proceeding with the dispensing of additional fluid(s) by the system.

The control element may be used to track the volume of the fluid(s) which have been dispensed as a way of tracking or approximating the volume of fluid(s) remaining and thereby providing data to trigger an indication that the user may desire to acquire additional fluid or to replenish/replace the reservoir. In one embodiment, the data may be coupled with a user account accessible by the networked device such that a product order request may be created and either submitted to a retailer automatically or provided to the user/account holder for review prior to placing the order for additional fluid(s).

The user interface may be used to track the performance of the system in terms of operating cycles, nozzle health, nozzle and fluid usage, parameter range and value selection, operating frequency, system power consumption and combinations of these as well as other operating parameters. In one embodiment, the user interface may enable the user or other individuals present in the environment served by the system to provide feedback to the system regarding the particular fluid combination(s) dispensed. The user interface may be expanded to allow other users with network capable devices access to the interface for the purpose of providing input on the dispensed combination. The feedback received may be used as input to the control logic to refine the operating parameter values and ranges over time as different randomly selected combinations are dispensed, perceived and commented upon. The feedback may as simple as an indication that he dispensed combination is acceptable or unacceptable, or the feedback interface may offer the option of indicating with more specificity which aspects of the dispensing were pleasing or unpleasant. In one embodiment, the various scent "note" dispensed may be indicated on the interface and the user may be afforded the opportunity to indicate if there was too much, too little, or an appropriate amount of the particular notes present in the combination dispensed.

In one embodiment, an overall system for dispensing fluids may comprise multiple sub-systems which cooperate to deliver fluid materials into the environment, or onto a substrate. The constituent sub-systems may communicate via a network interface disposed in electrical communication with the individual sub-system control elements in each the sub-systems.

The network interface may be one of the exemplary network interfaces described above. The constituent sub-systems may exchange information which, for example, may allow the overall composite system to coordinate fluid dispensing according to a schedule, or to start or stop dispensing at the command of one of the constituent control elements, or at the command of an (non-dispensing) external device which is also in communication with the network structure.

The constituent control elements may exchange information which may allow overall operating parameters, values of which may be selected at least partially in a random manner by the constituent system control elements, to remain within a defined working range when considered as a whole system.

For example, the relative ratios of the different fluids may be subject to random determination by at least some of the constituent control elements, while the relative ratio of the different fluids dispensed by the composite system may be limited by a set of constraints governing the composite system. Intra-system communication of the randomly selected parameters may result in the alteration of one or more of the constituent systems' behavior in order to operate the overall system within the system constraints in view of the randomly selected operational parameters communicated by some of the sub-systems.

In one embodiment, the overall parameters may require the dispensing of two fluids from the system. In this embodiment, a first subsystem may dispense all of the first fluid required and a second system may dispense all of the second fluid required. As another example, each of the first and second sub-systems may dispense only a portion of each of the required amounts of the first and second fluids with the total amount of each of the fluids meeting the required amounts to be dispensed. Communications over the network enables this dispensing without a high likelihood that the ratio of the first and second desired fluids will be outside the specified or desired ranges.

In another example, the firing frequencies or dispensing intervals of constituent dispensing systems may be shared among the constituent systems so that the frequencies or intervals can be ensured to be the same, or different as selected by the user, among the constituent systems, in order that the appearance of randomness by an external observer could be less or greater, respectively.

In another example, a non-dispensing device which is in communication with the network could serve a command function, supplying constraints under which the composite system must operate, or providing scheduling or other remote control functions, or providing parameters such as random number seed(s) which may serve to increase or decrease the amount of randomness of dispensing of the composite system as observed by an external observer. In this example, a user may communicate with the system to select operational parameters for dispensing according to defined needs. The time of day, activities in the environment, the number of people present in the environment etc. The remote control aspects of the system enable a user to direct the operation of the system as they are en-route to the environment. A user may activate the system and select operational parameters for their residence as they are travelling to their residence. In this embodiment, a first system on the network could be used to control a second system on the network.

As shown in the Figure, the system 1000, includes a plurality of fluid reservoirs 100. Each reservoir includes a fluid (not shown), and may include a memory element (not shown). The fluid reservoirs are in fluid communication with at least one MEMS dispensing element 200. A control element 300, comprising a memory element (not shown), is in electrical communication with each of the MEMS dispensing element 200, and a power supply element 400. A user interface is in electrical communication with the power supply 400 and the control element 300. The user interface 500, includes a switch 510 and optimally includes a networked device 520. The system further comprises a network interface element 600, and an environmental sensor 700.

A. A System for dispensing fluid materials, the system comprising:
 a. a plurality of fluid storage chambers, each of the plurality containing a stored fluid;
 b. at least one MEMS dispensing element disposed in fluid communication with at least one of the plurality of fluid storage chambers;
 c. a control element disposed in electrical communication with the at least one MEMS dispensing element and comprising a memory component;
 d. a power supply disposed in electrical communication with the at least one MEMS dispensing element and the control element;
 e. a user interface disposed in electrical communication with the control element;
wherein the memory component contains programmed instructions which, when executed by the control element cause the system to randomly dispense a first fluid from a first fluid storage chamber, and randomly disperse a second fluid from a second fluid storage chamber B. The system according to paragraph A, wherein the user interface comprises a switch in electrical communication with an input of the control element, the input having a switchable electrical state, the control element configured to read and execute the programmed instructions of the memory component as or after the input electrical state changes.

C. The system according to any one of paragraphs A, or B, wherein the memory component contains a plurality of distinct programmed instructions.

D. The system according to any one of paragraphs A, B, or C, further comprising a network interface disposed in electrical communication with the power supply and the control element.

E. The system according to any one of paragraphs A, B, C, or D, the user interface comprising a networked device disposed in communication with the network interface and a memory component comprising programmed instructions which, when executed cause the control element to store programmed instructions in the memory component of the control element according to input from the networked device.

F. The system according to any one of paragraphs A, B, C, D, or E, wherein the fluid storage chambers comprise a second memory component disposed in electrical communication with the control element, the memory component containing data associated with fluid contained in the fluid storage chamber.

G. The system according to any one of paragraphs A, B, C, D, E, or F, further comprising an environmental sensor.

H. The system according to paragraph G, wherein the environmental sensor comprises a proximity sensor.

I. The system according to any one of paragraphs D, E, F, or G, wherein the system controls a second system on the network.

Throughout this specification, components referred to in the singular are to be understood as referring to both a single unit or plurality of such component.

All percentages stated herein are by weight unless otherwise specified.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A system for dispensing fluid materials, the system comprising:
   a plurality of fluid storage chambers comprising a first fluid storage chamber containing a first perfume mixture and a second fluid storage chamber containing a second perfume mixture, wherein the first and second perfume mixtures are different;
   at least one micro electro-mechanical system ink jet head dispensing element disposed in fluid communication with the first and second fluid storage chambers;
   a control element disposed in electrical communication with the at least one micro electro-mechanical system ink jet head dispensing element, wherein said control element comprises programmable electronics and a memory component containing programmed instructions, wherein the programmed instructions comprise randomization calculations for randomly dispensing the first perfume mixture and the second perfume mixture, wherein randomly dispensing includes randomly selecting a ratio of the first perfume mixture to the second perfume mixture, and a frequency and a droplet size of each of the first perfume mixture and the second perfume mixture;
   a power supply disposed in electrical communication with the at least one micro electro-mechanical system ink jet head dispensing element and the control element; and
   a user interface disposed in electrical communication with the control element,
   wherein the system randomly dispenses the first perfume mixture from the first fluid storage chamber, and randomly dispenses the second perfume mixture from the second fluid storage chamber.

2. A system for dispensing fluid materials, the system comprising:
   a plurality of fluid storage chambers comprising a first fluid storage chamber containing a first perfume mixture and a second fluid storage chamber containing a second perfume mixture, wherein the first and second perfume mixtures are different;
   at least one micro electro-mechanical system dispensing element disposed in fluid communication with the first and second fluid storage chambers;
   a programmable electronic device disposed in electrical communication with the at least one micro electro-mechanical system dispensing element, wherein said programmable electronic device comprises programmable electronics and a memory component containing programmed instructions, wherein the programmed instructions comprise randomization calculations for randomly dispensing the first perfume mixture and the second perfume mixture, wherein randomly dispensing includes randomly selecting a ratio of the first perfume mixture to the second perfume mixture, a frequency and a droplet size of the first perfume mixture and the second perfume mixture;
   a power supply disposed in electrical communication with the at least one micro electro-mechanical system dispensing element and the control element; and
   a user interface disposed in electrical communication with the control element,
   wherein the system randomly dispenses the first perfume mixture from the first fluid storage chamber, and randomly dispenses the second perfume mixture from the second fluid storage chamber, and wherein a ratio of the first perfume mixture to the second perfume mixture, a frequency, and a droplet size are randomly calculated for each random dispersal of the first perfume mixture and the second perfume mixture.

3. A system for dispensing fluid materials, the system comprising:
   a plurality of fluid storage chambers comprising a first fluid storage chamber containing a first perfume mixture and a second fluid storage chamber containing a second perfume mixture, wherein the first and second perfume mixtures are different;
   at least one micro electro-mechanical system ink jet head dispensing element disposed in fluid communication with the first and second fluid storage chambers;
   a control element disposed in electrical communication with the at least one micro electro-mechanical system ink jet head dispensing element, wherein said control element comprises programmable electronics and a memory component containing programmed instructions, wherein the programmed instructions comprise randomization calculations for randomly dispensing the first perfume mixture and the second perfume mixture;
   a power supply disposed in electrical communication with the at least one micro electro-mechanical system ink jet head dispensing element and the control element; and
   a user interface disposed in electrical communication with the control element; wherein the user interface comprises a switch in electrical communication with an input of the control element, the input having a switchable electrical state, the control element configured to read and execute the programmed instructions of the memory component as or after the input electrical state changes, thereby causing the system to randomly dispense the first perfume mixture from the first fluid storage chamber, and randomly dispense the second perfume mixture from the second fluid storage chamber, and wherein randomly dispensing includes randomly selecting a ratio of the first perfume mixture to the second perfume mixture, a frequency and a droplet size of the first perfume mixture and the second perfume mixture.

4. The system according to claim 3, wherein the fluid storage chambers comprise a second memory component disposed in electrical communication with the control element, the second memory component containing data associated with fluid contained in the fluid storage chambers.

5. The system according to claim 3, further comprising an environmental sensor.

6. The system according to claim 5, wherein the environmental sensor comprises a proximity sensor.

7. The system of claim 3, further comprising a network interface disposed in electrical communication with the power supply and the control element.

8. The system according to claim 7, the user interface comprising a networked smart device or phone disposed in communication with the network interface and configured to cause the control element to store programmed instructions in the memory component of the control element according to input from the networked smart device or phone.

* * * * *